United States Patent
Luo et al.

(10) Patent No.: US 6,565,879 B1
(45) Date of Patent: *May 20, 2003

(54) TOPICAL AND TRANSDERMAL ADMINISTRATION OF PEPTIDYL DRUGS WITH HYDROXIDE-RELEASING AGENTS AS SKIN PERMEATION ENHANCERS

(75) Inventors: Eric C. Luo, Plano, TX (US); Eric C. Jacobson, San Diego, CA (US); Tsung-Min Hsu, San Diego, CA (US)

(73) Assignee: Dermatrends, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/687,937

(22) Filed: Oct. 13, 2000

Related U.S. Application Data

(63) Continuation-in-part of application No. 09/569,889, filed on May 11, 2000, which is a continuation-in-part of application No. 09/465,098, filed on Dec. 16, 1999.

(51) Int. Cl.$^7$ .......................... A61F 13/00; A61L 15/00
(52) U.S. Cl. ..................... 424/449; 424/443; 424/445; 424/447; 424/448; 514/946; 514/947; 514/944
(58) Field of Search .................... 424/449, 443, 424/448; 514/944, 946, 945

(56) References Cited

U.S. PATENT DOCUMENTS

| | | |
|---|---|---|
| 4,789,547 A | 12/1988 | Song et al. |
| 4,837,027 A | 6/1989 | Lee et al. |
| 4,940,456 A | 7/1990 | Sibalis et al. |
| 5,032,109 A | 7/1991 | Sibalis |
| 5,071,657 A | 12/1991 | Oloff et al. |
| 5,250,023 A | 10/1993 | Lee et al. |
| 5,432,192 A | 7/1995 | Sawanishi et al. |
| 5,446,070 A | 8/1995 | Mantelle |
| 5,449,670 A | 9/1995 | Skinner et al. |
| 5,462,744 A * | 10/1995 | Gupte et al. .................. 424/448 |
| 5,462,746 A | 10/1995 | Wolter et al. |
| 5,474,783 A | 12/1995 | Miranda et al. |
| 5,498,417 A | 3/1996 | Lhila et al. |
| 5,534,496 A | 7/1996 | Lee et al. |
| 5,562,917 A | 10/1996 | Durif et al. |
| 5,599,554 A | 2/1997 | Majeti |
| 5,807,568 A | 9/1998 | Cody et al. |
| 5,830,497 A * | 11/1998 | Yamanaka et al. .......... 424/448 |
| 5,834,513 A | 11/1998 | Ptchelintsev et al. |
| 5,847,003 A | 12/1998 | Ptchelintsev et al. |
| 5,863,555 A | 1/1999 | Heiber et al. |
| 5,939,094 A | 8/1999 | Durif et al. |
| 5,962,018 A | 10/1999 | Curtis et al. |
| 5,985,317 A | 11/1999 | Venkateshwaran et al. |
| 5,989,586 A | 11/1999 | Hsu et al. |
| 5,990,113 A | 11/1999 | Yamazaki et al. |
| 5,990,179 A | 11/1999 | Gyory et al. |
| 5,993,851 A | 11/1999 | Foldvari |
| 5,998,368 A | 12/1999 | Gozes et al. |
| 6,002,961 A | 12/1999 | Mitragotri et al. |
| 6,004,566 A | 12/1999 | Friedman et al. |
| 6,019,988 A * | 2/2000 | Parab et al. ................ 424/400 |
| 6,019,997 A | 2/2000 | Scholz et al. |
| 6,197,331 B1 * | 3/2001 | Lerner et al. ................ 424/443 |

FOREIGN PATENT DOCUMENTS

| | | |
|---|---|---|
| EP | 0709088 | 5/1996 |
| FR | 2692145 | * 12/1993 |
| JP | 2180835 | 7/1990 |
| WO | WO 99/49844 | 10/1999 |

OTHER PUBLICATIONS

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

* cited by examiner

*Primary Examiner*—Thurman K. Page
*Assistant Examiner*—Isis Ghali
(74) *Attorney, Agent, or Firm*—Dianne E. Reed; Shelley P. Eberle; Reed & Eberle LLP

(57) ABSTRACT

A method is provided for increasing the permeability of skin or mucosal tissue to a topically or transdermally administered pharmacologically or cosmeceutically active peptide, polypeptide or protein. The method involves use of a specified amount of a hydroxide-releasing agent, the amount optimized to increase the flux of the peptide, polypeptide or protein through a body surface while minimizing the likelihood of skin damage, irritation or sensitization. Formulations and drug delivery devices employing hydroxide-releasing agents as permeation enhancers are provided as well.

50 Claims, No Drawings

TOPICAL AND TRANSDERMAL ADMINISTRATION OF PEPTIDYL DRUGS WITH HYDROXIDE-RELEASING AGENTS AS SKIN PERMEATION ENHANCERS

CROSS-REFERENCE TO RELATED APPLICATIONS

This is a continuation-in-part of U.S. Ser. No. 09/569,889, filed May 11, 2000 which is a continuation-in part of U.S. Ser. No. 09/465,098, filed Dec. 16, 1999, the disclosures of which are incorporated by reference.

TECHNICAL FIELD

This invention relates generally to topical and transdermal administration of pharmacologically active peptidyl drugs, and more particularly relates to methods and compositions for administering peptidyl drugs transdermally.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation, degradation of certain drugs via gastrointestinal enzymes and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration. With many drugs, the rate of permeation through the skin is extremely low and is particularly problematic for high molecular weight drugs such as peptides, polypeptides and proteins. Consequently, a means for enhancing the permeability of the skin is desired to effect transport of the drug into and through intact skin.

In order to increase the rate at which a drug penetrates through the skin, then, various approaches have been followed, each of which involves the use of either a chemical penetration enhancer or a physical penetration enhancer. Physical enhancement of skin permeation includes, for example, electrophoretic techniques such as iontophoresis. The use of ultrasound (or "phonophoresis") as a physical penetration enhancer has also been researched. Chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are innocuous compounds that serve merely to facilitate diffusion of the drug through the stratum corneum.

Various compounds for enhancing the permeability of skin are known in the art and described in the pertinent texts and literature. Compounds that have been used to enhance skin permeability include: sulfoxides such as dimethylsulfoxide (DMSO) and decylmethylsulfoxide ($C_{10}MSO$); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450; see also); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate ("PEGML"; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; organic acids, particularly salicylic acid and salicylates, citric acid and succinic acid; and certain peptides, e.g., peptides having Pro-Leu at the N-terminus and followed by a protective group (see U.S. Pat. No. 5,534,496). *Percutaneous Penetration Enhancers*, eds. Smith et al. (CRC Press, 1995) provides an excellent overview of the field and further background information on a number of chemical and physical enhancers.

Although many chemical permeation enhancers are known, there is an ongoing need for an enhancer that (1) is highly effective in increasing the rate at which a pharmacologically active agent permeates the skin, and (2) does not result in skin damage, irritation, sensitization, or the like. In particular, there is a need for a chemical permeation enhancer that enables the transdermal administration of high molecular weight drugs such as peptidyl drugs.

SUMMARY OF THE INVENTION

It is thus a primary object of the invention to address the above-described need in the art by providing a method for transdermally administering a pharmacologically active peptide, polypeptide or protein.

It is another object of the invention to provide such a method wherein a hydroxide-releasing agent is employed as a permeation enhancer to increase the flux of a pharmacologically active peptide, polypeptide or protein through a patient's skin or mucosal tissue.

It is still another object of the invention to provide such a method wherein the amount of hydroxide-releasing agent employed is optimized to enhance permeation while minimizing or eliminating the possibility of skin damage, irritation or sensitization.

It is a further object of the invention to provide such a method wherein the active agent is a cosmeceutically effective agent.

It is an additional object of the invention to provide formulations and drug delivery systems for carrying out the aforementioned methods.

Additional objects, advantages and novel features of the invention will be set forth in part in the description that follows, and in part will become apparent to those skilled in the art upon examination of the following, or may be learned by practice of the invention.

In one aspect of the invention, the invention pertains to a method for topically or transdermally administering a peptidyl drug, by administering the drug and a hydroxide-releasing agent to the body surface of the individual. The hydroxide-releasing agent is administered in an amount and for a time period such that upon administration of the peptidyl drug, the flux of the drug through the skin is enhanced, thus facilitating treatment of a peptidyl drug-responsive condition or disease. The amount of the hydroxide-releasing agent, however, is an amount that will not cause damage to skin or injury to the patient. Typically, a "patch" is used to administer the active agent, in which case the drug and hydroxide-releasing agent are present in one or more drug reservoirs. However, the peptidyl drug and hydroxide-releasing agent may also be administered using a liquid or semisolid formulation, e.g., as a water-based cream or gel as will be discussed in further detail below. In addition, the peptidyl drug and hydroxide-releasing agent may be co-administered, i.e., administered together, or may be administered separately as in, for example, "pretreatment" of an individual's body surface with the hydroxide-releasing agent followed by administration of the peptidyl drug.

In another aspect of the invention, the invention pertains to a composition of matter useful for the delivery of a peptidyl drug through a body surface. The composition comprises an aqueous formulation of a therapeutically effective amount of a peptidyl drug and a hydroxide-releasing agent in an amount effective to enhance the flux of the peptidyl drug through the body surface without causing damage thereto. In addition, the composition includes a pharmaceutically acceptable carrier suitable for topical or transdermal peptidyl drug administration.

In yet another aspect of the invention, a system for the topical or transdermal administration of a peptidyl drug is provided comprising at least one peptidyl drug reservoir, a means for maintaining the system in drug and enhancer transmitting relationship to the body surface, and an occlusive backing layer to serve as the outer surface of the device during use. The peptidyl drug reservoir(s) contain both the peptidyl drug and a hydroxide-releasing agent. The hydroxide-releasing agent is present in an amount to enhance the flux of the drug through the body surface without causing damage to the skin or injury to the patient.

The peptidyl drug incorporated as part of the invention may be any peptidyl drug that provides a desired pharmacological effect. General categories of such peptidyl drugs include, for example, coagulation modulators, cytokines, endorphins, hormones, analogues of LHRH (luteinizing hormone-releasing hormone) and kinins.

DETAILED DESCRIPTION OF THE INVENTION

Definitions and Overview

Before describing the present invention in detail, it is to be understood that this invention is not limited to specific drug delivery systems, device structures, enhancers or carriers, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "peptidyl drug" includes a mixture of two or more such drugs, reference to "a hydroxide-releasing agent" includes mixtures of two or more hydroxide-releasing agents, and the like.

In describing and claiming the present invention, the following terminology will be used in accordance with the definitions set out below.

Amino acid residues in peptides described herein are abbreviated as follows: glutamine is Gln or Q; leucine is Leu or L; methionine is Met or M; and proline is Pro or P.

Stereoisomers (e.g., D-amino acids) of conventional amino acids, unnatural amino acids such as α,α-disubstituted amino acids, N-alkyl amino acids, lactic acid, and other unconventional amino acids may also be present in the peptidyl drugs that can be administered using the method. Examples of unconventional amino acids include, without limitation, β-alanine, 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, nor-leucine, and other similar amino acids and imino acids (e.g., 4-hydroxyproline).

The terms "active agent," "drug" and "pharmacologically active agent" are used interchangeably herein to refer to a compound or composition of matter which, when administered to an organism (human or animal), induces a desired pharmacologic, physiologic and/or cosmeceutical effect by local or systemic action. The active agents herein are peptidyl drugs and derivatives and analogs of those compounds or classes of compounds specifically mentioned which also induce the desired effect.

A "peptidyl drug" as used herein is an active agent, drug or pharmacologically active agent that comprises a peptide, polypeptide or protein. Pharmacologically active derivatives and fragments of peptidyl drugs are included as well. For ease of discussion, a "peptidyl drug" will also include a single amino acid and derivatives thereof.

A "peptide" refers to a polymer in which the monomers are amino acids linked together through amide bonds. "Peptides" are generally smaller than proteins, i.e., about two to about ten amino acids in length. The term "peptide" includes "dipeptides" comprised of two amino acids and "tripeptides" comprised of three consecutively linked amino acids, and so forth.

A "polypeptide" refers to a polymer of amino acids generally comprised of about ten to about fifty amino acids.

A "protein" as used herein refers to a polymer of amino acids conventionally comprised of over fifty amino acids. The proteins that may be used as peptidyl drugs in the present invention may be naturally occurring proteins, modified naturally occurring proteins, or chemically synthesized proteins that may or may not be identical to naturally occurring proteins.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient or individual, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be one that is acted upon chemically in an aqueous environment to generate hydroxide ions (e.g., a metal carbonate).

By "therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream so as to achieve therapeutically effective blood levels, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug or pharmacologically active agent to the skin or mucosa, as in, for example, the treatment of various skin disorders. Topical administration, in contrast to transdermal administration, provides a local rather than a systemic effect.

The term "body surface" is used to refer to skin or mucosal tissue.

By "predetermined area" of skin or mucosal tissue, which refers to the area of skin or mucosal tissue through which a drug-enhancer formulation is delivered, is intended a defined area of intact unbroken living skin or mucosal tissue. That area will usually be in the range of about 5 $cm^2$ to about 200 $cm^2$, more usually in the range of about 5 $cm^2$ to about 100 $cm^2$, preferably in the range of about 20 $cm^2$ to about 60 $cm^2$. However, it will be appreciated by those skilled in the art of drug delivery that the area of skin or mucosal tissue through which drug is administered may vary significantly, depending on patch configuration, dose, and the like.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example a Franz diffusion apparatus as known in the art and as employed in the Examples herein.

An "effective" amount of a permeation enhancer is meant a nontoxic, nondamaging but sufficient amount of the enhancer to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art which are nontoxic and do not interact with other components of the composition in a deleterious manner.

The term "aqueous" refers to a formulation or drug delivery system that contains water or that becomes water-containing following application to the skin or mucosal tissue.

In one embodiment, then, the invention pertains to a method for treating an individual with a peptidyl drug-responsive condition or disease comprising administering a peptidyl drug and a hydroxide releasing agent to the body surface of the individual. The method increases the rate at which the peptidyl drug permeates through the body surface of a patient without causing damage thereto. Typically, a "patch" will be used to administer the active agent, in which case the drug and hydroxide-releasing agent are present in a drug reservoir. However, the drug and hydroxide-releasing agent may also be administered using a liquid or semisolid formulation, e.g., as a water-based cream or gel as will be discussed in further detail below. Alternatively, or in addition, the body surface may be pretreated with the enhancer, e.g., treated with a dilute aqueous solution of the hydroxide-releasing agent prior to administration of the peptidyl drug. When the hydroxide-releasing agent is administered to the body surface prior to administering the peptidyl drug, it is preferred that the hydroxide-releasing agent is administered up to about 24 hours, more preferably about 15 hours, and most preferably about 5 hours, prior to administering the peptidyl drug. Drug delivery may be either topical or transdermal.

The Hydroxide-Releasing Agent

The "hydroxide-releasing agent" is a chemical compound that releases free hydroxide ions in the presence of an aqueous fluid. Therefore, any patch that is used should have an occlusive backing, or contain water, or both. Similarly, any liquid or semisolid formulation that is used should be aqueous or used in conjunction with an overlayer of an occlusive material.

Any hydroxide-releasing agent may be used provided that the compound releases free hydroxide ions in the presence of an aqueous fluid. Examples of suitable hydroxide-releasing agents include, but are not limited to, inorganic hydroxides, inorganic oxides and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium carbonate, sodium phosphate (tribasic), sodium phosphate (dibasic), sodium borate, potassium carbonate, potassium acetate, potassium phosphate (dibasic), potassium phosphate (tribasic), sodium metaborate, and the like. Preferred hydroxide-releasing agents are metal hydroxides such as sodium hydroxide and potassium hydroxide.

It is important that the amount of hydroxide-releasing agent in any patch or formulation is optimized so as to increase the flux of the drug through the body surface while minimizing any possibility of skin damage. Generally, this means that the amount of hydroxide-releasing agent will represent about 0.25 wt. % to 7.0 wt. %, preferably 0.5 wt. % to 4.0 wt. %, more preferably 0.75 wt. % to 2.0 wt. % and optimally about 1.0 wt. %, of a topically applied formulation or of a drug reservoir of a drug delivery system, or "patch." The aforementioned amount applies to formulations and patches in which the drug does not react with the hydroxide-releasing agent and where there are no additional species in the formulation or patch that could react with or be neutralized by the hydroxide-releasing agent. These amounts also apply to aqueous solutions of hydroxide-releasing agents employed as a pretreatment, i.e., an aqueous solution of the hydroxide-releasing agent applied to the body surface prior to administering the peptidyl drug.

For formulations and patches in which the active peptidyl drug can react with the hydroxide-releasing agent, and/or wherein there are additional species in the formulations or systems that can be neutralized by or react with the hydroxide-releasing agent (i.e., acidic inactive ingredients), the amount of hydroxide-releasing agent will be the total of (1) the amount necessary to neutralize or react with the drug and/or other base-neutralizable species, plus (2) about 0.25 wt. % to 7.0 wt. %, preferably 0.5 wt. % to 4.0 wt. %, more preferably 0.75 wt. % to 2.0 wt. % and optimally about 1.0 wt. %, of the formulation or drug reservoir. That is, for peptidyl drugs that react, e.g., undergo hydrolysis, with the hydroxide-releasing agent, the hydroxide-releasing agent should be present in an amount just sufficient to neutralize the drug, plus an additional amount (i.e., 0.25 wt. % to 7.0 wt. %, preferably 0.5 wt. % to 4.0 wt. %, more preferably 0.75 wt. % to 2.0 wt. % and optimally about 1.0 wt. %) to enhance the flux of the drug through the skin or mucosal tissue. For patches, the aforementioned percentages are given relative to the total dry weight of the formulation components and the adhesive, gel or liquid reservoir.

In general, it is preferred that the pH of the body surface in contact with a formulation or drug delivery system of the invention (i.e., the interface between the body surface and the formulation or delivery system) be in the range of approximately 8.5 to 13, preferably 8.5 to 11.5. Similarly, it is preferred that the pH of the formulation or the drug composition contained within a delivery system be in the range of approximately 8.5 to 13, preferably 8.5 to 11.5.

The Peptidyl Drug

The peptidyl drug is any pharmacologically active peptide, polypeptide or protein. Once chosen, the peptidyl drug must be prepared or obtained from commercial suppliers for incorporation in the delivery system. The peptidyl drug may be prepared using standard synthetic techniques, recombinant technology or extraction from natural sources.

Synthetic production of peptides, polypeptides and proteins generally employs techniques of standard solid phase peptide synthesis well known in the art. In such a method, the synthesis is sequentially carried out by incorporating the desired amino acid residues one at a time onto a growing peptide chain according to the general principles of solid phase synthesis as described, for example, by Merrifield (1963) *J. Amer. Chem. Soc.* 85:2149–2154. Common to chemical syntheses of peptides, polypeptides and proteins is the protection of reactive side chain groups of the various amino acid moieties with suitable protecting groups which will prevent a chemical reaction from occurring at that site until the protecting group is ultimately removed. It is also well known to protect the α-amino group on an amino acid while that entity reacts at the carboxyl group, followed by the selective removal of the α-amino protecting group to allow a subsequent reaction to take place at that site. Examples of suitable α-amino and side chain protecting groups are well known in the art.

Alternatively, the peptide, polypeptide or protein may be prepared by employing recombinant technology via techniques well known in the art. That is, conventional recombinant techniques may be used, which, as will be appreciated by those skilled in the art, involves constructing DNA encoding the desired amino acid sequence, cloning the DNA into an expression vector, transforming a host cell, e.g., a bacterial, yeast, or mammalian cell, and expressing the DNA to produce the desired peptide, polypeptide or protein.

Additionally, the peptides, polypeptides or proteins can be obtained from natural sources such as a human or other animal, and may be extracted from either a living organism or from a cadaver. The material is separated and purified prior to incorporation into a drug delivery system or dosage form. Techniques of separation and purification are well known in the art and include, for example, centrifugation and chromatography.

The peptidyl drug administered may be any compound that is suitable for topical or transdermal delivery and induces a desired local or systemic effect. Such substances include the broad classes of compounds normally delivered through body surfaces and membranes, including skin. In general, this includes: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; antiarrhythmic agents; central nervous system stimulants; cough and cold preparations, including decongestants; diuretics; genetic materials; hormonolytics; hypnotics; hypoglycemic agents; immunosuppressive agents; leukotriene inhibitors; mitotic inhibitors; muscle relaxants; narcotic antagonists; nutritional agents such as essential amino acids; ophthalmic drugs such as antiglaucoma agents; parasympatholytics; psychostimulants; sedatives; sympathomimetics; tranquilizers; and vasodilators including general coronary, peripheral and cerebral.

Although any peptidyl drug may be incorporated into the delivery systems of the present invention, the drug is generally selected from coagulation factors, cytokines, endorphins, kinins, hormones, LHRH (luteinizing hormone-releasing hormone) analogs and other peptidyl drugs that provide a desired pharmacological activity. Of course, the categories provided are not intended to be limiting and simply serve as a means for organization. As will be appreciated, a peptidyl drug may fall into more than one category.

The peptidyl drug in the delivery system of the present invention may be a coagulation modulator (or derivative thereof). Many coagulation modulators are endogenous proteins that circulate in the blood and interact with other endogenous proteins to control blood coagulation. Preferred coagulation modulators include $\alpha_1$-antitrypsin, $\alpha_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, thrombomodulin and combinations thereof. When applicable, both the "active" and "inactive" versions of these proteins are included.

The cytokines are a large and heterogeneous group of proteins and may serve as the peptidyl drug in the delivery system of the present invention. Cytokines are immunoregulatory proteins and have a role in the function of the immune system and the control of hematopoiesis, i.e., the production of blood or blood cells. Preferred cytokines include colony stimulating factor 4, heparin binding neurotrophic factor (HBNF), interferon-α, interferon α-2a, interferon α-2b, interferon α-n3, interferon-β, interferon-γ, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), thymopoietin and combinations thereof.

Endorphins or pharmacologically active derivatives thereof may be included in the delivery systems of the invention. Endorphins are generally peptides or small-chain peptides that activate opiate receptors. Agonist and antagonist derivatives of the naturally-occurring endophins are also contemplated. Representative examples of endorphins or pharmacologically active derivatives include dermorphin, dynorphin, α-endorphin, β-endorphin, γ-endorphin, σ-endorphin [Leu$^5$]enkephalin, [Met$^5$]enkephalin, substance P, and combinations thereof.

Many hormones are derived from peptides. The peptidyl hormones that may be present in the delivery systems described herein may be naturally occurring or may be pharmacologically active derivatives of known hormones. In addition, the peptidyl hormones may be human or be derived from other animal sources. Examples of peptidyl hormones for incorporation in the present invention include activin, amylin, angiotensin, atrial natriuretic peptide (ANP), calcitonin (derived from chicken, eel, human, pig, rat, salmon, etc.), calcitonin gene-related peptide, calcitonin N-terminal flanking peptide, cholecystokinin (CCK), ciliary neurotrophic factor (CNTF), corticotropin (adrenocorticotropin hormone, ACTH), cortotropin-releasing factor (CRF or CRH), epidermal growth factor (EGF), follicle-stimulating hormone (FSH), gastrin, gastrin inhibitory peptide (GIP), gastrin-releasing peptide, ghrelin, glucogon, gonadotropin-releasing factor (GnRF or GNRH), growth hormone releasing factor (GRF, GRH), human chorionic gonadotropin (hCH), inhibin A, inhibin B, insulin (derived from beef, human, pig, etc.), leptin, lipotropin (LPH), luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, triiodothyronine, vasoactive intestinal peptide (VIP), vasopressin (antidiuretic hormone, ADH) and combinations thereof.

Particularly preferred analogues of LHRH include buserelin, deslorelin, fertirelin, goserelin, histrelin, leuprolide (leuprorelin), lutrelin, nafarelin, tryptorelin and combinations thereof.

In addition, the peptidyl drug may be a kinin. Particularly preferred kinins include bradykinin, potentiator B, bradykinin potentiator C, kallidin and combinations thereof.

Still other peptidyl drugs that provide a desired pharmacological activity can be incorporated into the delivery systems of the invention. Examples include abarelix, adenosine deaminase, anakinra, ancestim, alteplase, alglucerase, asparaginase, bivalirudin, bleomycin, bombesin, desmopressin acetate, des-Q14-ghrelin, dornase-α, enterostatin, erythropoeitin, exendin-4, fibroblast growth factor-2, filgrastim, β-glucocerebrosidase, gonadorelin, hyaluronidase, insulinotropin, lepirudin, magainin I, magainin II, nerve growth factor, pentigetide, thrombopoietin, thymosin α-1, thymidin kinase (TK), tissue plasminogen activator, tryptophan hydroxylase, urokinase, urotensin II and combinations thereof.

Particularly preferred systemically active agents that can be administered transdermally in conjunction with the present invention include oxytocin, insulin and LHRH analogues, such as leuprolide.

Preferred agents for local, topical administration are within the broad classes of compounds known to be topically administrable, including, but not limited to, topical antibiotics (e.g., magainin I and magainin II), anti-fungal agents, anti-psoriatic agents, antipruritic agents, antihistamines, antineoplastic agents (e.g., asparaginase and bleomycin), local anesthetics, anti-inflammatory agents and the like.

The peptidyl drug may be administered, if desired, in the form of a salt, ester, amide, prodrug, derivative, or the like, provided the salt, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992). Suitable acids for preparing acid addition salts include both organic acids, e.g., acetic acid, propionic acid, glycolic acid pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, basic. salts of acid moieties are prepared using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups present within the molecular structure of the drug. The esters are typically acyl-substituted derivatives of free alcohol groups, i.e., moieties which are derived from carboxylic acids of the formula RCOOH where R is alkyl, and preferably is lower alkyl. Amides and prodrugs may also be prepared using techniques known to those skilled in the art or described in the pertinent literature. Prodrugs are typically prepared by covalent attachment of a moiety which results in a compound that is therapeutically inactive until modified by an individual's metabolic system.

The active agent administered also may be one that is cosmetically or "cosmeceutically" effective rather than pharmacologically active. Such agents include, for example, compounds that can reduce the appearance of aging or photodamaged skin, e.g., and/or cosmetically acceptable salts, esters, amides, or other derivatives thereof.

Formulations

The method of delivery of the peptidyl drug may vary, but necessarily involves application of a hydroxide-releasing agent either prior to, e.g., when pretreating the body surface, or simultaneously with application of the peptidyl drug. Both the hydroxide-releasing agent and the peptidyl drug are applied (either together or separately) to a predetermined area of the skin or other tissue for a period of time sufficient to provide the desired local or systemic effect. The method may involve direct application of a composition containing the hydroxide-releasing agent and/or peptidyl drug as an ointment, gel, cream, or the like, or may involve use of a drug delivery device. In either case, water must be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during administration of the hydroxide-releasing agent, and optimally, during administration of the peptidyl drug. Consequently, the hydroxide-releasing agent and the peptidyl drug (either together or separately) may be incorporated into a suitable formulation and applied to the skin surface or incorporated into a drug delivery system, e.g., a "patch."

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy,* 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those drugs having an unusually low rate of permeation through the skin or mucosal tissue, it may be desirable to include a second permeation enhancer in the formulation in addition to the hydroxide-releasing agent. Such enhancers include, for example, the following: sulfoxides such as dimethylsulfoxide (DMSO) and decylmethylsulfoxide ($C_{10}MSO$); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450; see also); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, diethanolamine, diethanolamine and triethanolamine; terpenes; alkanones; and organic acids, particularly salicylic acid and salicylates, citric acid and succinic acid. As noted earlier herein, *Percutaneous Penetration Enhancers*, eds. Smith et al. (CRC Press, 1995) provides an excellent overview of the field and further information concerning possible secondary enhancers for use in conjunction with the present invention.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. Preferred formulations will typically contain on the order of about 0.5 wt. % to 50 wt. %, optimally about 10 wt. % to 30 wt. %, active agent.

Drug Delivery Systems

An alternative and preferred method involves the use of a drug delivery system, e.g., a topical or transdermal "patch," wherein the active agent is contained within a laminated structure that is to be affixed to the skin. In such a structure, the drug composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene(polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of drug to be delivered and the flux of the drug through the body surface. Larger patches will be necessary to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, the peptidyl drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device.

As with the topically applied formulations of the invention, the composition containing drug and hydroxide-releasing agent within the drug reservoir(s) of these laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

Utility

Peptidyl drugs are powerful agents used to treat a variety of conditions or diseases. The clinical use of peptidyl drugs includes, for example, replacement or augmentation of a naturally occurring protein in an individual suffering from a lack of that particular protein. Peptidyl drugs may also possess antagonistic activity, so as to reduce, for example, the action of a naturally occurring peptide or protein causing an undesirable physiological effect. In addition, peptidyl drugs such as the peptidyl endorphins may be employed as agents to alleviate pain.

The amount of drug administered and present in the formulations and drug delivery systems of the invention is an amount required to achieve an effective therapeutic result. Such an amount depends on many factors, such as the minimum necessary dosage of the drug for the particular indication being treated; the solubility and permeability of the carrier and adhesive layer; and the period of time for which the hydroxide releasing-agent and/or device will be affixed to the skin or other body surface. The minimum amount of drug is determined by the requirement that a sufficient quantity of drug must be present in the device to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

The invention accordingly provides a novel and highly effective means for increasing the flux of a peptidyl agent through the body surface (skin or mucosal tissue) of a human or animal. The hydroxide-releasing agents discussed herein, employed in specific amounts. relative to a solution, formulation or drug reservoir, may be used as permeation enhancers with a variety of peptidyl drugs. Surprisingly, the increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the materials of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

An in vitro skin permeation study was conducted using three leuprolide solutions. The formulations used to prepare these systems are listed in Table 1, which include weight and weight percent of each ingredient in the formulations. The weight of sodium hydroxide was 0 g, 0.0125 g, and 0.0275 g for formulation #Leu-S1, #Leu-S2 and #Leu-S3, respectively. Each formulation was stirred until the solution was uniform.

The in-vitro permeation of each leuprolide solution through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The skin was clamped between the donor and receiver chambers of the diffusion cell, and the stratum corneum was allowed to dry. The leuprolide solution was applied to the stratum corneum using a micro-pipette. Each formulation was applied in a 25 $\mu$l dosage and a 50 $\mu$l dosage for a total of 6 test groups. The receiver chamber was sealed to the atmosphere using parafilm wrap so that it was spill-proof and airtight. Three diffusion cells were used for each test group for a total of 18 cells.

The cells were filled with deionized (DI) water for a receiver solution. The DI water had been degased to remove air bubbles. The receiver solution was completely withdrawn and replaced with fresh DI water at each time point. Samples of the receiver solution were taken and analyzed by HPLC (high pressure liquid chromatography) to determine the leuprolide concentration. The cumulative amount of leuprolide across human cadaver skin (Table 2) was calculated using the measured leuprolide concentrations in the receiver solutions for each time point.

TABLE 1

Weight and Weight Percent of Each Ingredient Based on Total Solution Weight for Three Leuprolide Transdermal Systems

|  | Leu-S1 | Leu-S2* | Leu-S3* |
|---|---|---|---|
| Leuprolide | 0.003 g (0.4%) | $6.4 \times 10^{-4}$ g (0.18%) | $6.4 \text{ g} \times 10^{-4}$ g (0.16%) |
| DI water | 0.45 g (64.0%) | 0.28 g (80.9%) | 0.33 g (80.3%) |
| NaOH | 0 g (0.0%) | 0.0125 g (3.6%) | 0.0275 g (6.7%) |
| Propylene Glycol | 0.25 g (35.6%) | 0.053 g (15.3%) | 0.053 g (13.0%) |

*Solutions Leu-S2 and Leu-3 were prepared using 0.15 g of Leu-S1, then adding the correct amount of NaOH and DI water. Percentages may not add up to 100% due to rounding.

TABLE 2

Cumulative Amount of Leuprolide Permeated Across Human Cadaver Skin From a 25 $\mu$l and a 50 $\mu$l Solution Containing NaOH at 5-hour and 24-hour Time Points ($\mu g/cm^2$)

|  | Leu-S1 25 $\mu$l | Leu-S2 25 $\mu$l | Leu-S3 25 $\mu$l | Leu-S1 50 $\mu$l | Leu-S2 50 $\mu$l | Leu S3 50 $\mu$l |
|---|---|---|---|---|---|---|
| 5 hours | 0.38 | 0.52 | 0.58 | 0.32 | 0.62 | 0.3 |
| 24 hours | 0.52 | 3.21 | 4.43 | 0.32 | 8.58 | 10.8 |

The cumulative amount of leuprolide across human cadaver skin for the 25 $\mu$l dosage at 24 hours increased from 0.52 $\mu g/cm^2$ to 4.43 $\mu g/cm^2$ when the calculated sodium hydroxide concentration in the dried patch was increased from 0% to 6.7%. The cumulative amount of leuprolide across human cadaver skin for the 50 $\mu$l dosage at 24 hours increased from 0.32 $\mu g/cm^2$ to 10.8 $\mu g/cm^2$ when the calculated sodium hydroxide concentration in the leuprolide solution was increased from 0% to 6.7%. The cumulative amount of leuprolide across human cadaver skin at 24 hours from the 50 $\mu$l dosage group containing 3.6% NaOH (Leu-S2) was 8.58 $\mu g/cm^2$, which was about 27 times higher than that from the formulation without NaOH (0.32 $\mu g/cm^2$, #Leu-S1).

EXAMPLE 2

The in-vitro permeation of oxytocin through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The skin was clamped between the donor and receiver chambers of the diffusion cell. Eighteen diffusion cells were used in this study. A 2% NaOH aqueous solution (50 $\mu$l) was introduced to the donor chambers of nine cells (cells #1 to 9) and a 4% NaOH aqueous solution (50 $\mu$l) was introduced to the donor chambers of the other nine cells (cells #10 to 18). Once the NaOH solution is applied, the donor chamber was covered with parafilm.

After 5 hours, the NaOH solution was washed away from the skin for 3 cells (cells #1 to 3) that were treated with 2% NaOH solution and 3 cells (cells #10 to 12) that were treated with 4% NaOH solution. After 10 hours, the NaOH solution was washed away from the skin for 3 cells (cells #4 to 6) that were treated with 2% NaOH solution and 3 cells (cells #13 to 15) that were treated with 4% NaOH solution. After 24 hours, the NaOH solution was washed away from the skin for 3 cells (cells #7 to 9) that were treated with 2% NaOH solution and 3 cells (cells #16 to 18) that were treated with 4% NaOH solution. To wash away the NaOH solution, the receiving fluid was removed and replaced with fresh DI water. This was done twice. DI water was added to the donor chamber to dilute the NaOH solution and then the donor solution was removed. This was repeated several times.

After the NaOH solution was washed away from the skin, the solution in the donor chamber was completely removed and replaced by 50 $\mu$l of an oxytocin solution. The formulation of the oxytocin solution is listed in Table 3. Once the oxytocin solution is applied, the donor chamber was covered with parafilm.

The cells were filled with DI water as a receiver solution. The DI water had been degased to remove air bubbles. The receiver solution was completely withdrawn and replaced with fresh DI water at each time point. The samples taken were analyzed by HPLC for the concentration of oxytocin in the receiver solution. The cumulative amount of oxytocin across human cadaver skin was calculated using the measured oxytocin concentrations in the receiver solutions for each time point, which were listed in Table 4.

TABLE 3

Formulation for the Oxytocin Solution

| Oxytocin | 0.005 g |
|---|---|
| DI water | 0.6 g |
| Propylene Glycol | 0.6 g |

TABLE 4

Cumulative Amount of Oxytocin Permeated Across Human Cadaver Skin From an Oxytocin Solution ($\mu g/cm^2$)

|  | Skin pretreated by 4% NaOH for 5 hr | Skin pretreated by 4% NaOH for 15 hr | Skin pretreated by 4% NaOH for 24 hr |
| --- | --- | --- | --- |
| 5 hours | 118.95 | 202.28 | 193.82 |
| 15 hours | 200.66 | 222.45 | 232.72 |
| 24 hours | 225.52 | 231.58 | 236.80 |

EXAMPLE 3

The in-vitro permeation of oxytocin through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The skin was clamped between the donor and receiver chambers of the diffusion cell. Eighteen diffusion cells were used in this study. A 0.25% NaOH aqueous solution (50 $\mu l$) was introduced to the donor chambers of nine cells (cells #1 to 9) and A 1.0% NaOH aqueous solution (50 $\mu l$) was introduced to the donor chambers of the other nine cells (cells #10 to 18). Once the NaOH solution is applied, the donor chamber was covered with parafilm.

After 5 hours, the NaOH solution was washed away from the skin for 3 cells (cells #1 to 3) that were treated with 0.5% NaOH solution and 3 cells (cells #10 to 12) that were treated with 1.0% NaOH solution. After 11 hours, the NaOH solution was washed away from the skin for 3 cells (cells #4 to 6) that were treated with 0.25% NaOH solution and 3 cells (cells #13 to 15) that were treated with 1.0% NaOH solution. After 24 hours, the NaOH solution was washed away from the skin for 3 cells (cells #7 to 9) that were treated with 0.25% NaOH solution and 3 cells (cells #16 to 18) that were treated with 1.0% NaOH solution. To wash away the NaOH solution, the receiving fluid was removed and replaced with fresh DI water. This was done twice. DI water was added to the donor chamber to dilute the NaOH solution and then the donor solution was removed. This was repeated several times until the pH of donor solution was less than 8.

After the NaOH solution was washed away from the skin, the solution in the donor chamber was completely removed and replaced by 50 $\mu l$ of an oxytocin solution. The formulation of the oxytocin solution is listed in Table 5. Once the oxytocin solution is applied, the donor chamber was covered with parafilm.

The cells were filled with DI water as a receiver solution. The DI water has been degased to remove air bubbles. The receiver solution was completely withdrawn and replaced with fresh DI water at each time point. The samples taken were analyzed by an HPLC for the concentration of oxytocin in the receiver solution. The cumulative amount of oxytocin across human cadaver skin was calculated using the measured oxytocin concentrations in the receiver solutions for each time point, which were listed in Table 6.

TABLE 5

Formulation for the Oxytocin Solution

| Oxytocin | 0.005 g |
| --- | --- |
| DI water | 0.6 g |
| Propylene Glycol | 0.6 g |

TABLE 6

Cumulative Amount of Oxytocin Permeated Across Human Cadaver Skin From an Oxytocin Solution ($\mu g/cm^2$)

|  | Skin pretreated by 1.0% NaOH for 5 hr | Skin pretreated by 1.0% NaOH for 11 hr | Skin pretreated by 1.0% NaOH for 24 hr |
| --- | --- | --- | --- |
| 4.25 hours | 0.45 | 53.42 | 13.23 |
| 14.75 hours | 0.97 | 67.97 | 21.06 |
| 24 hours | 0.97 | 75.36 | 30.97 |

What is claimed is:

1. A method for enhancing the flux of a peptidyl drug through a body surface of an individual so as to achieve therapeutically effective blood levels thereof, the method comprising administering a peptidyl drug and a predetermined amount of a hydroxide-releasing agent to the body surface of the individual, wherein the predetermined amount of the hydroxide-releasing agent is effective to provide a pH in the range of approximately 8.5 to 13 at the localized region of the body surface, during drug administration, and wherein the peptidyl drug and hydroxide-releasing agent are present in a formulation and the amount of hydroxide-releasing agent in the formulation applied to the body surface is the total of (a) the amount required to neutralize any acidic species in the formulation plus (b) an mount equal to approximately 0.25 wt. % to 7.0 wt. % of the formulation.

2. The method of claim 1, wherein the body surface is skin.

3. The method of claim 1, wherein the body surface is mucosal tissue.

4. The method of claim 1, wherein the formulation is a liquid or semi-solid formulation.

5. The method of claim 4, wherein the formulation is aqueous.

6. The method of claim 5, wherein the formulation has a pH in the range of approximately 8.5 to 13.

7. The method of claim 6, wherein the formulation has a pH in the range of approximately 8.5 to 11.5.

8. The method of claim 5, wherein the aqueous formulation is a cream or gel.

9. The method of claim 1, wherein the amount of hydroxide-releasing agent in the formulation is the total of (a) the amount required to neutralize any acidic species in the formulation plus (b) an amount equal to approximately 0.5 wt. % to 4.0 wt. % of the formulation.

10. The method of claim 9, wherein the amount of hydroxide-releasing agent in the formulation is the total of (a) the amount required to neutralize any acidic species in the formulation plus (b) an amount equal to approximately 0.75 wt. % to 2.0 wt. % of the formulation.

11. The method of claim 9, wherein the amount of hydroxide-releasing agent in the formulation is the total of (a) the amount required to neutralize any acidic species in the formulation plus (b) an amount equal to approximately 1.0 wt. % of the formulation.

12. The method of claim 1, wherein the peptidyl drug and hydroxide-releasing agent are administered by applying a drug delivery device to a predetermined area of a human patient's body surface, the device comprising the peptidyl drug and the hydroxide-releasing agent, and having an outer occlusive backing layer that serves as the outer surface of the device during use.

13. The method of claim 12, wherein the peptidyl drug and hydroxide-releasing agent are present in an adhesive, gel or liquid formulation contained within the device.

14. The method of claim 1, which further comprises pretreating the body surface with a pretreatment amount of the hydroxide-releasing agent prior to administering the peptidyl drug and hydroxide-releasing agent formulation.

15. The method of claim 14, wherein the pretreatment hydroxide-releasing agent is administered up to about 24 hours prior to administering the peptidyl drag and hydroxide-releasing agent formulation.

16. The method of claim 15, wherein the pretreatment hydroxide-releasing agent is administered up to about 15 hours prior to administering the peptidyl drug and hydroxide-releasing agent are present in a formulation.

17. The method of claim 16, wherein the pretreatment hydroxide-releasing agent is administered up to about 5 hours prior to administering the peptidyl drug and hydroxide-releasing agent are present in a formulation.

18. The method of claim 14, wherein the pretreatment hydroxide-releasing agent is administered to the body in the form of a solution comprised of approximately 0.25 wt. % to 7.0 wt. % of the hydroxide-releasing agent.

19. The method of claim 18, wherein the pretreatment hydroxide-releasing agent is administered to the body in the form of a solution comprised of approximately 0.5 wt. % to 4.0 wt. % of the hydroxide-releasing agent.

20. The method of claim 19, wherein the pretreatment hydroxide-releasing agent is administered to the body in the form of a solution comprised of approximately 0.75 wt. % to 2.0 wt. % of the hydroxide-releasing agent.

21. The method of claim 20, wherein the pretreatment hydroxide-releasing agent is administered to the body in the form of a solution comprised of approximately 1.0 wt. % of the hydroxide-releasing agent.

22. The method of claim 1, wherein the peptidyl drug is a peptide.

23. The method of claim 1, wherein the peptidyl drug is a polypeptide.

24. The method of claim 1, wherein the peptidyl drug is a protein.

25. The method of claim 1, wherein the peptidyl drug is selected from the group consisting of coagulation modulators, cytokines, endorphins, kinins, peptidyl hormones, LHRH analogues and combinations thereof.

26. The method of claim 25, wherein the peptidyl drug is a coagulation modulator.

27. The method of claim 26, wherein the peptidyl drug is selected from the group consisting of $\alpha_1$-antitrypsin, $\alpha_2$-macroglobulin, antithrombin III, factor I, factor II, factor III, factor V, factor VII, factor VIII, factor IX, factor X, factor XI, factor XII, heparin cofactor II, kallikrein, plasmin, plasminogen, prekallikrein, protein C, protein S, thrombomodulin and combinations thereof.

28. The method of claim 25, wherein the peptidyl drug is a cytokine.

29. The method of claim 28, wherein the peptidyl drug is selected from the group consisting of colony stimulating factor 4, heparin binding neurotrophic factor, interferon-$\alpha$, interferon $\alpha$-2a, interferon $\alpha$-2b, interferon $\alpha$-n3, interferon-$\beta$, interferon-$\gamma$, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, tumor necrosis factor, tumor necrosis factor-$\alpha$, granuloycte colony-stimulating factor, granulocyte-macrophage colony-stimulating factor, macrophage colony-stimulating factor, midkine, thymopoietin and combinations thereof.

30. The method of claim 25, wherein the peptidyl drug is an endorphin.

31. The method of claim 30, wherein the peptidyl drug is selected from the group consisting of dermorphin, dynorphin, $\alpha$-endorphin, $\beta$-endorphin, $\gamma$-endorphin, ($\sigma$-endorphin [Leu$^5$]enkephalin, [Met$^5$]enkephalin, substance P, and combinations thereof.

32. The method of claim 25, the peptidyl drug is a kinin.

33. The method of claim 32, wherein the peptidyl drug is selected from the group consisting of bradykinin, potentiator B, bradykinin potentiator C, kallidin and combinations thereof.

34. The method of claim 25, wherein the peptidyl drug is a peptidyl hormone.

35. The method of claim 34, wherein the peptidyl drug is selected from the group consisting of activin, amylin, angiotensin, atrial natriuretic peptide, calcitonin, calcitonin gene-related peptide, calcitonin N-terminal flanking peptide, cholecystokinin, ciliary neurotrophic factor, corticotropin, corticotropin-releasing factor, epidermal growth factor, follicle-stimulating hormone, gastrin, gastrin inhibitory peptide, gastrin-releasing peptide, ghrelin, glucogon, gonadotropin-releasing factor, growth hormone releasing factor, human chorionic gonadotropin, inhibin A, inhibin B, insulin, leptin, lipotropin, luteinizing hormone, luteinizing hormone-releasing hormone, $\alpha$-melanocyte-stimulating hormone, $\beta$-melanocyte-stimulating hormone, $\gamma$-melanocyte-stimulating hormone, melatonin, motilin, oxytocin, pancreatic polypeptide, parathyroid hormone, placental lactogen, prolactin, prolactin-release inhibiting factor, prolactin-releasing factor, secretin, somatotropin, somatostatin, thyrotropin, thyrotropin-releasing factor, thyroxine, triiodothyronine, vasoactive intestinal peptide, vasopressin and combinations thereof.

36. The method of claim 35, wherein the peptidyl drug is oxytocin.

37. The method of claim 25, wherein the peptidyl drug is an LHRH analogue.

38. The method of claim 37, wherein the peptidyl drug is selected from the group consisting of buserelin, deslorelin, fertirelin, goserelin, histrelin, leuprolide, lutrelin, nafarelin, tryptorelin and combinations thereof.

39. The method of claim 38, wherein the peptidyl drug is leuprolide.

40. The method of claim 1, wherein the peptidyl drug is selected from the group consisting of abarelix, adenosine deaminase, anakinra, ancestim, alteplase, alglucerase, asparaginase, bivalirudin, bleomycin, bombesin, desmopressin acetate, des-Q14-ghrelin, dornase-$\alpha$, enterostatin, erythropoeitin, exendin-4, fibroblast growth factor-2, filgrastim, $\beta$-glucocerebrosidase, gonadorelin, hyaluronidase, insulinotropin, lepirudin, magainin I, magainin II, nerve growth factor, pentigetide, thrombopoietin, thymosin $\alpha$-1, thymidin kinase, tissue plasminogen activator, tryptophan hydroxylase, urokinase, urotensin II and combinations thereof.

41. The method of claim 1, wherein the hydroxide-releasing agent is selected from the group consisting of inorganic hydroxides, inorganic oxides, metal salts of weak acids, and mixtures thereof.

42. The method of claim 41, wherein the hydroxide-releasing agent is an inorganic hydroxide.

43. The method of claim 42, wherein the inorganic hydroxide is selected from the group consisting of ammonium hydroxide, alkali metal hydroxides, alkaline earth metal hydroxides, and mixtures thereof.

44. The method of claim 43, wherein the inorganic hydroxide is selected from the group consisting of ammonium hydroxide, sodium hydroxide, calcium hydroxide, potassium hydroxide, magnesium hydroxide, and mixtures thereof.

45. The method of claim 44, wherein the inorganic hydroxide is sodium hydroxide.

46. The method of claim 44, wherein the inorganic hydroxide is potassium hydroxide.

47. The method of claim 41, wherein the hydroxide-releasing agent is an inorganic oxide.

48. The method of claim 47, wherein the inorganic oxide is selected from the group consisting of magnesium oxide, calcium oxide, and mixtures thereof.

49. The method of claim 41, wherein the hydroxide-releasing agent is a metal salt of a weak acid.

50. The method of claim 49, wherein the metal salt of a weak acid is selected from the group consisting of sodium acetate, sodium carbonate, tribasic sodium phosphate, dibasic sodium phosphate, sodium borate, potassium carbonate, potassium acetate, dibasic potassium phosphate, tribasic potassium phosphate, sodium metaborate, and mixtures thereof.

* * * * *

UNITED STATES PATENT AND TRADEMARK OFFICE
CERTIFICATE OF CORRECTION

PATENT NO. : 6,565,879 B1
DATED : May 20, 2003
INVENTOR(S) : Eric C. Luo, Eric C. Jacobson and Tsung-Min Hsu It is certified that error appears in the above-identified patent and that said Letters Patent is hereby corrected as shown below:

Column 20,
Line 27, please delete "mount" and insert -- amount --.

Column 21,
Line 7, please delete "drag" and insert -- drug --.

Column 22,
Line 4, please delete "(".

Signed and Sealed this

Twenty-third Day of September, 2003

JAMES E. ROGAN
*Director of the United States Patent and Trademark Office*